US012673145B2

(12) United States Patent
Wegener

(10) Patent No.: US 12,673,145 B2
(45) Date of Patent: Jul. 7, 2026

(54) SYSTEMS AND METHODS FOR BLOOD PROCESSING WITH A REMOTE COMPUTING DEVICE

(71) Applicant: Fenwal, Inc., Lake Zurich, IL (US)

(72) Inventor: Christopher J. Wegener, Libertyville, IL (US)

(73) Assignee: Fenwal, Inc., Lake Zurich, IL (US)

( * ) Notice: Subject to any disclaimer, the term of this patent is extended or adjusted under 35 U.S.C. 154(b) by 775 days.

(21) Appl. No.: 17/938,216

(22) Filed: Oct. 5, 2022

(65) Prior Publication Data

US 2023/0103528 A1     Apr. 6, 2023

Related U.S. Application Data

(60) Provisional application No. 63/252,735, filed on Oct. 6, 2021.

(51) Int. Cl.
*A61M 1/30*          (2006.01)
*A61M 1/36*          (2006.01)

(52) U.S. Cl.
CPC .......... *A61M 1/303* (2014.02); *A61M 1/3693* (2013.01)

(58) Field of Classification Search
CPC ...... A61M 1/303; A61M 1/3693; G16H 40/67
See application file for complete search history.

(56) References Cited

U.S. PATENT DOCUMENTS

| | | | |
|---|---|---|---|
| 5,868,696 A | 2/1999 | Giesler | |
| 2003/0154108 A1 | 8/2003 | Fletcher-Haynes | |
| 2006/0026205 A1* | 2/2006 | Butterfield | G16H 20/10 |
| 2016/0235901 A1* | 8/2016 | Miller | A61M 1/36 |
| 2016/0328521 A1* | 11/2016 | Mickles | G16H 10/60 |
| 2018/0015418 A1 | 1/2018 | Binninger | |

FOREIGN PATENT DOCUMENTS

WO          2020055958 A1     3/2020

OTHER PUBLICATIONS

European Search Report and Opinion Issued by the European Patent Office for Application No. 22199692.9, dated Oct. 2, 2023 (9 pages total).

* cited by examiner

*Primary Examiner* — Susan S Su
(74) *Attorney, Agent, or Firm* — Cook Alex Ltd.

(57) ABSTRACT

Systems and methods are provided for separating blood components from whole blood. A blood processing device, as part of a blood processing system, has a controller configured to operate the blood processing device based on a plurality of collection protocols. The blood processing device is wirelessly connected to a remote computing device configured to maintain a plurality of collection protocols. At least one additional computing device is configured to update one or more of the plurality of collection protocols on said remote computing device by communicating changes to a protocol maintained on the remote computing device which updates the plurality of collection protocols at the controller of the blood processing device.

11 Claims, 5 Drawing Sheets

SYSTEMS AND METHODS FOR BLOOD PROCESSING WITH A REMOTE COMPUTING DEVICE

CROSS-REFERENCE TO RELATED APPLICATIONS

This application claims the benefit of and priority to U.S. Provisional Patent Application Ser. No. 63/252,735, filed Oct. 6, 2021, the contents of which are incorporated by reference herein.

BACKGROUND

Field of the Disclosure

The invention relates to blood processing. More particularly, the invention relates to systems and methods for collecting blood components during a collection procedure based on collection protocols from remote computing devices.

Description of Related Art

Various blood processing systems make it possible to separate blood into two or more constituent parts, which may be useful for donation purposes and for treatment of individuals with potentially detrimental or harmful blood conditions or disorders.

When such systems are used for blood component donation, whole blood is typically drawn from a donor, the particular blood component or constituent is removed and collected, and the remaining blood constituents are returned to the donor.

Such systems can also be used to provide blood components for cellular therapies to patients or individuals. For these therapies it is typical to separate a particular cellular or other blood component and modify, enrich and/or expand the collected component before returning it to the patient as part of a therapeutic treatment. For example, one such therapy, Chimeric antigen receptor (CAR) T-cell therapy, alters a patients T-cells and adds an artificial receptor to the cells that attach to cancer cell antigens. These modified T-cells are returned to the patient and can help destroy specific cancer cells.

These modified therapeutic cells are produced in manufacturing facilities separate from the blood collection site. In providing modified cells that are effective for a particular therapy, the manufacturing facilities will typically have requirements and/or preferences for the collected cells, including, but not limited to, the manner and conditions in which they are collected.

The manufacturing labs or facilities described above typically do not own or control the collection facilities where the cells are collected. The cell collection equipment such as apheresis devices (which are commercially available from several different providers) is generally owned, maintained and operated by the collection facilities, not the therapy cell manufacturer. Currently the manufacturers have designated SOPs (Standard Operating Procedures) for collection facilities and protocols that the collections should follow to ensure that the desired cells are collected in the proper way so as to make them suitable for modification and ultimate use in therapeutic treatments.

In many cases there are differences in the protocol used to collect cells depending on the manufacturing facility and the type of drug therapy that is going to be provided. This may include differences in specific blood component to be collected, the apheresis equipment to be used for such collection, and/or collection parameters such as total blood processed volume or harvest offsets. At present, it is the primary responsibility of the collection facility to ensure that the correct protocols are used and followed for a specified collection and that the apheresis equipment is updated with the most current protocols provided by the therapy provider.

It would, therefore, be desirable to provide or have available a system and method these manufacturers can better and more easily ensure that the blood component or components have been collected in accordance with the correct and updated collection protocols such that the collected cells are able to be effectively utilized by their facility in creating the modified cellular therapy product for a specific therapy. It would also be desirable to provide methods and systems whereby the collection facility is relieved of having to update individual apheresis equipment with the desired current protocols. In that regard, it would be beneficial for a method and system that can be updated remotely without manual input at the collection site.

SUMMARY

There are several aspects of the present subject matter which may be embodied separately or together in the devices and systems described and claimed below. These aspects may be employed alone or in combination with other aspects of the subject matter described herein, and the description of these aspects together is not intended to preclude the use of these aspects separately or the claiming of such aspects separately or in different combinations as set forth in the claims appended hereto.

In one aspect, a blood processing system is provided. The system includes a blood processing device with a controller configured to operate the blood processing device based on a plurality of collection protocols, a remote computing device wirelessly connected to the blood processing device, and at least one additional computing device. The remote computing device is configured to maintain a plurality of collection protocols. The at least one additional computing device is configured to update one or more of the plurality of collection protocols on said remote computing device by communicating changes to a protocol maintained on the remote computing device which updates the plurality of collection protocols at the controller of the blood processing device.

In another aspect, a method of collecting blood components from a donor is provided. The method includes providing a collection protocol to a computing device, communicating the collection protocol from said computing device to a remote computing device, communicating the collection protocol from said remote computing device to a controller of a blood processing device, selecting a collection protocol from an interface on the blood processing device, connecting the blood processing device to a patient; and starting the blood collection based on the selected collection protocol.

DESCRIPTION OF THE ILLUSTRATED EMBODIMENTS

The embodiments disclosed herein are for the purpose of providing a description of the present subject matter, and it is understood that the subject matter may be embodied in various other forms and combinations not shown in detail. Therefore, specific designs and features disclosed herein are not to be interpreted as limiting the subject matter as defined in the accompanying claims.

The disclosure will be more fully understood from the following description taken in conjunction with the accompanying drawings. Some of the figures may have been simplified by the omission of selected elements for the purpose of more clearly showing other elements. Such omissions of elements in some figures are not necessarily indicative of the presence or absence of particular elements in any of the exemplary embodiments, except as may be explicitly delineated in the corresponding written description. None of the drawings is necessarily to scale.

Figure 1:
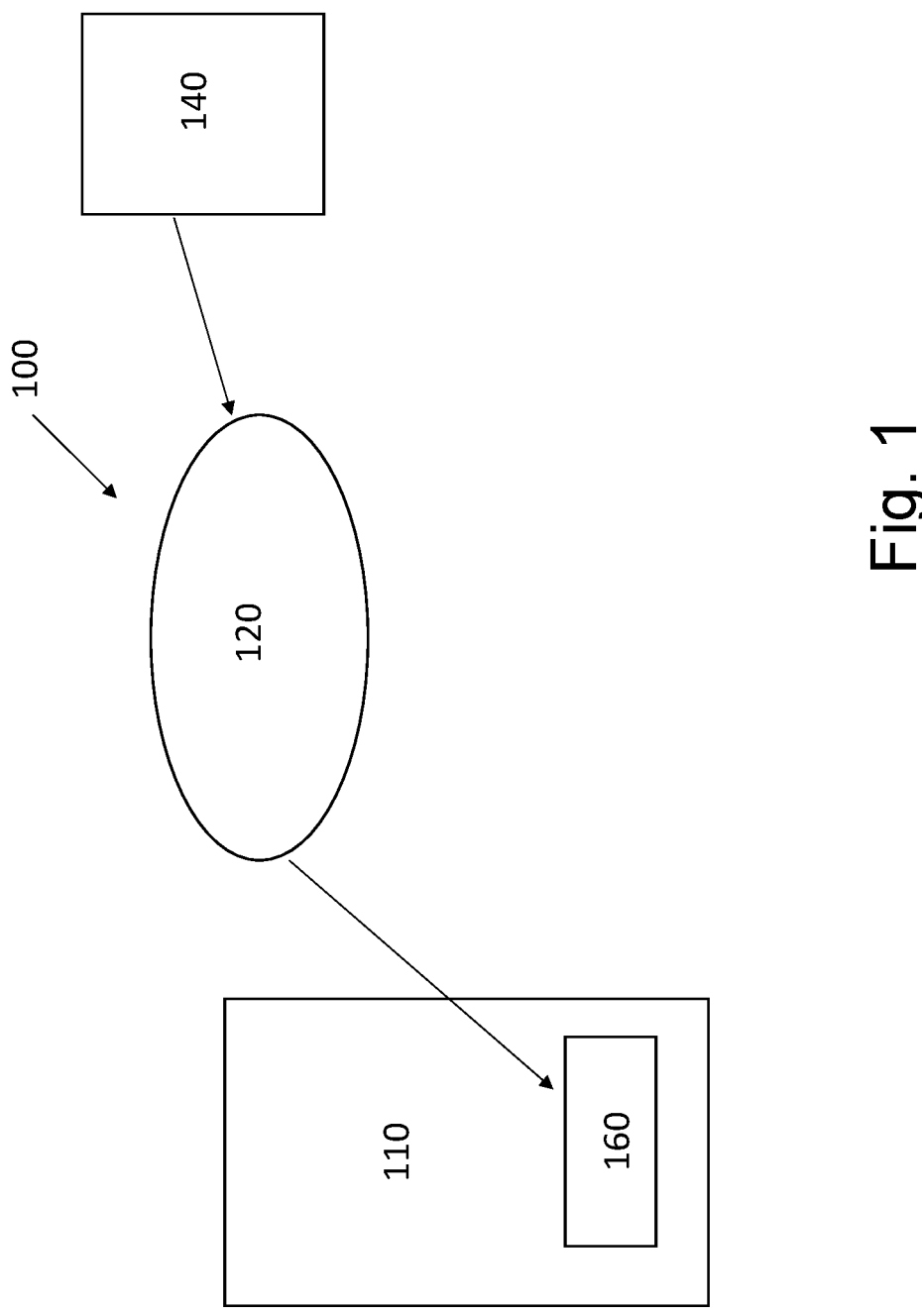
FIG. 1 is a is a schematic view of an exemplary blood processing system.
Figure 2:
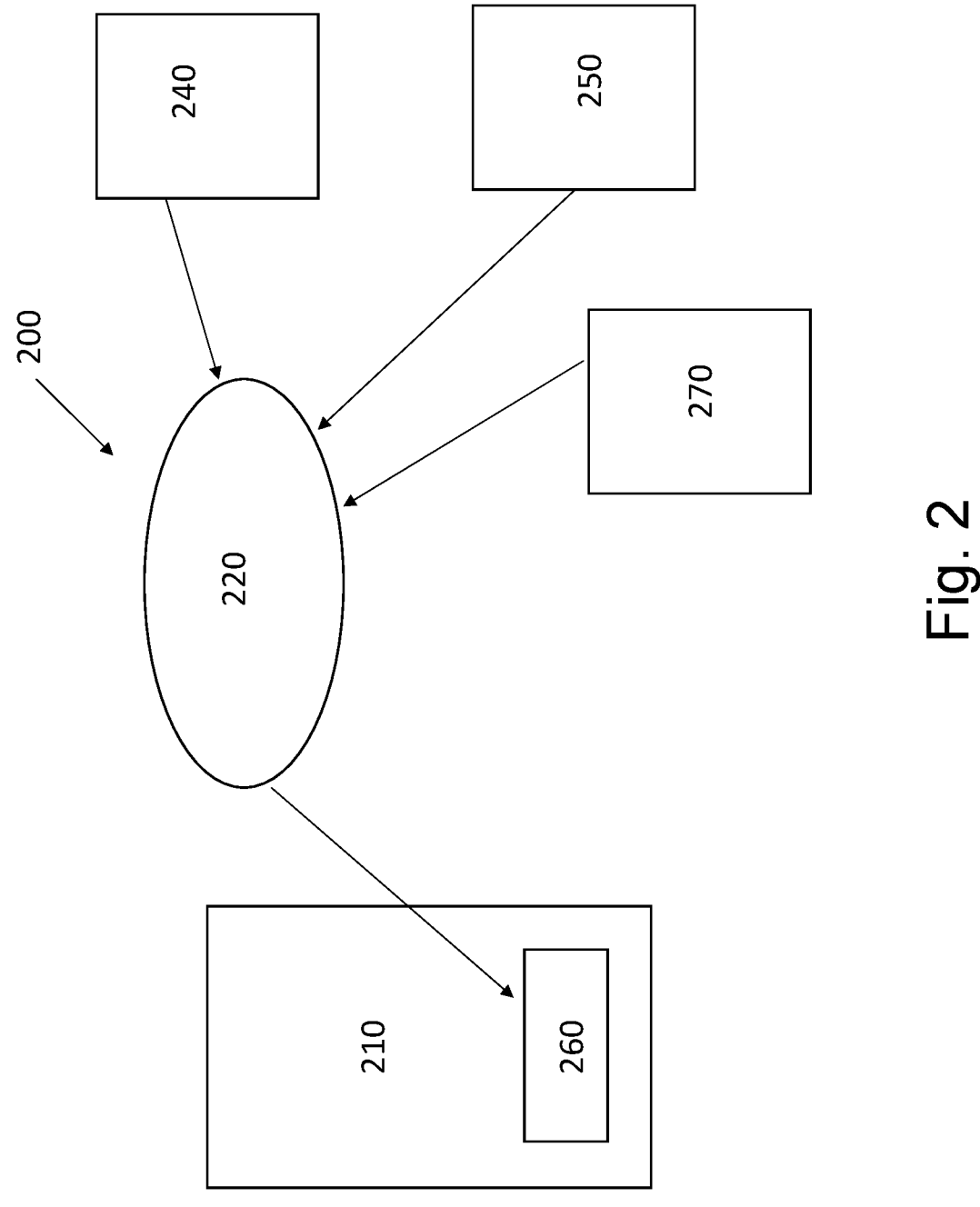
FIG. 2 is a schematic view of another exemplary blood processing system.

As illustrated in FIGS. 1 and 2, blood processing system 100, 200 includes a blood processing device 110, 210 to receive a biological fluid to be processed, a control unit (or controller) 160, 260 coupled to the blood processing device 110, 210, the controller 160, 260 configured to operate the blood processing device 110, 210 according to a blood collection or separation procedure or process.

According to certain embodiments, the controllers 160, 260 may be in communication with a remote computing device 120, 220 as part of a (computerized) system, the remote computing device being used as a point of centralized data management and retention. The system also includes an additional computing device or devices 140, 240, 250, 270 which also communicates with the remote computing device.

Before the centralized data management and/or control of the blood processing device or instruments that define, in part, the system and methods are discussed, a brief description of the blood processing devices 110, 210 that define the system is provided below so that the different features of the centralized data management and/or control can be appreciated. For example, although a detailed discussion of apheresis devices is beyond the scope of the present disclosure, it will be helpful to understand the blood processing device and the controller 160, 260 and how the system and the controller 160, 260 cooperate to perform a blood separation procedure.

Blood processing systems and methods according to the current disclosure are described as utilizing a blood processing device or system, such as specifically an apheresis device or system. However, it should be understood that the principles described herein are not limited to a particularly configured device and/or a particular sequence of steps or stages. Rather, the blood processing systems and methods described herein may be applied using a variety of differently configured blood processing devices (such as the described AMICUS® and TRIMA ACCEL® systems) that carry out blood collection and/or blood component procedures in different ways. Indeed, it is contemplated that the principles described herein may be applied to any blood processing device.

Whole blood is typically separated into its constituents through centrifugation. This requires that the whole blood be passed through a centrifuge after it is withdrawn from, and before it is returned to, the source. To avoid contamination of the blood and possible infection of the source (if the source is a living donor or patient), the blood is preferably contained within a sealed, sterile fluid flow system during the entire centrifugation process. Typical blood processing devices thus include a permanent, reusable centrifuge assembly containing the hardware (drive system, pumps, valve actuators, programmable controller, and the like) that spins and pumps the blood, and a disposable, sealed and sterile fluid processing assembly that is mounted in cooperation on the hardware. The centrifuge assembly engages and spins a disposable separation chamber of the fluid processing assembly during a collection or treatment procedure. The blood, however, makes actual contact only with the fluid processing assembly, which assembly is used only once and then discarded.

Figure 4:
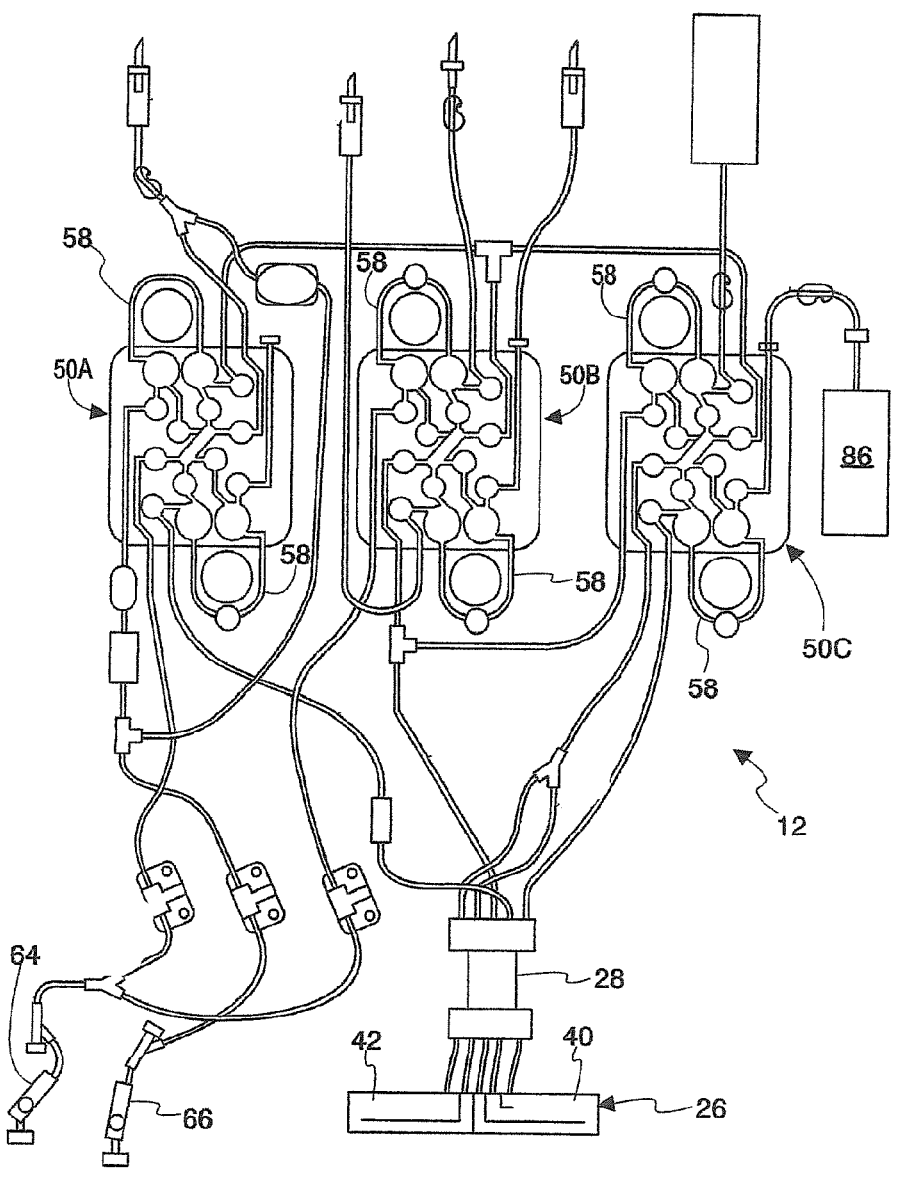
FIG. 4 is a diagrammatic view of an exemplary disposable fluid flow circuit that may be used in combination with the blood separation device of FIG. 3.
Figure 5:
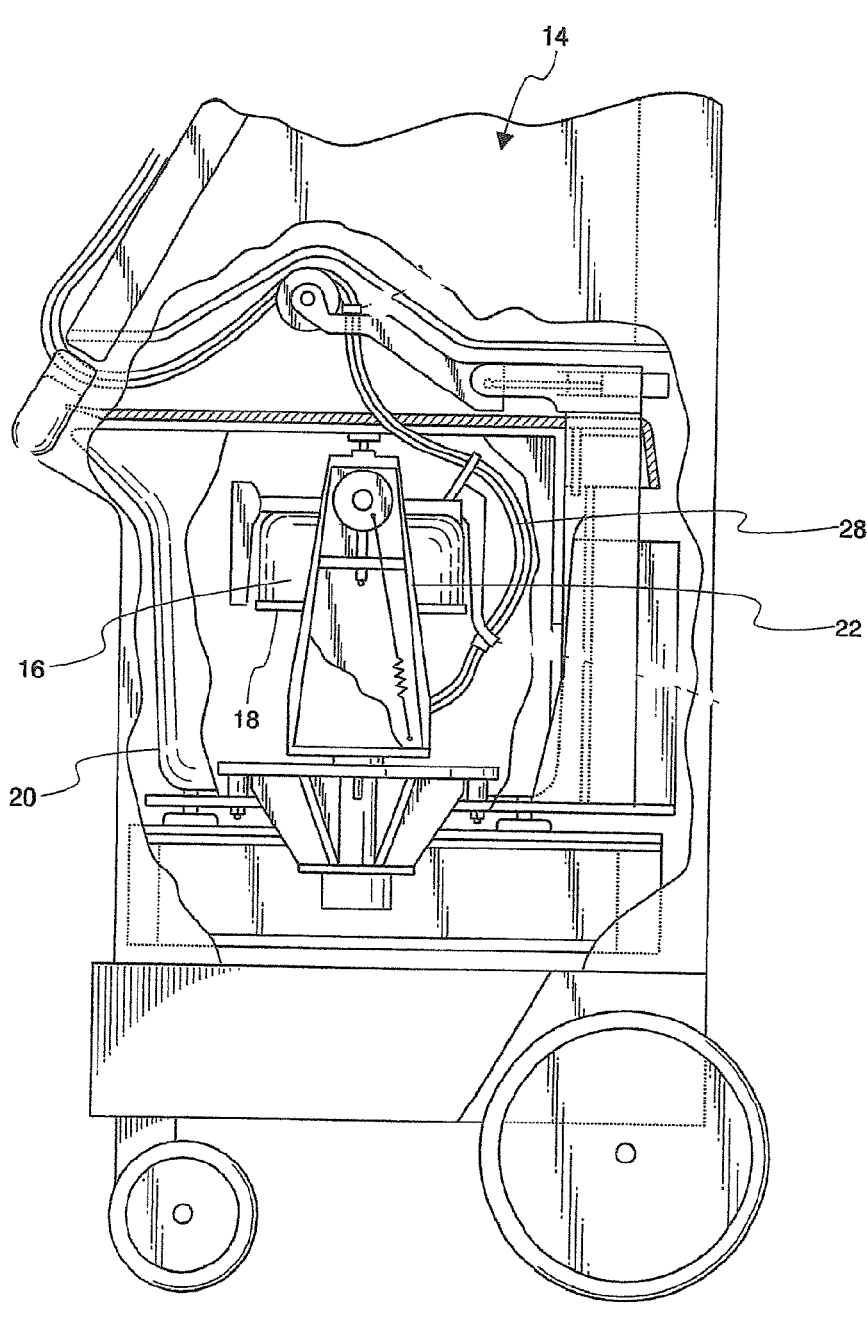
FIG. 5 is a side elevation view, with portions broken away and in section, of the blood separation device of FIG. 3, with a centrifuge bowl and spool of the device being shown in their operating position and with the fluid flow circuit of FIG. 4 mounted thereon.

Centrifugal blood separation devices are known in the art and currently practiced commercially. One known separation device is shown in FIGS. 3-5.

Figure 3:
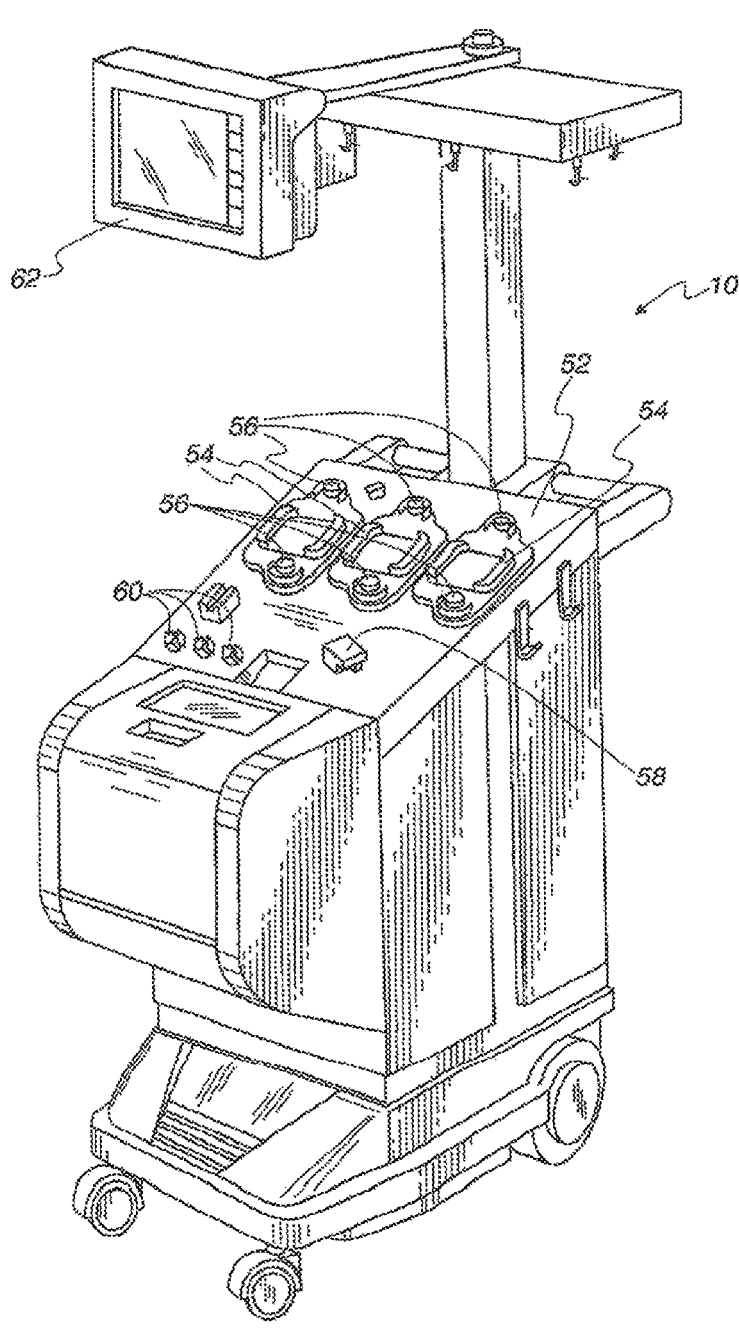
FIG. 3 is a is a perspective view of an exemplary commercial blood separation device.

FIG. 3 shows an exemplary commercial centrifugal blood separation device 10 that may be used in combination with a disposable fluid flow circuit 12 (FIG. 4) to comprise a blood processing device (FIG. 5) for separating blood into two or more components. The illustrated blood separation device 10 is currently marketed as the AMICUS® separator by Fenwal, Inc. of Lake Zurich, Ill., which is an affiliate of Fresenius Kabi AG of Bad Homburg, Germany, and is described in greater detail in U.S. Pat. No. 5,868,696, which is hereby incorporated herein by reference. The device 10 can be used for processing various fluids, but is particularly well suited for processing whole blood, blood components, or other suspensions of biological cellular materials.

The blood processing device 110, 210 includes a controller, such as the controller 160, 260 shown in FIGS. 1 and 2. The controller may, according to the embodiments, include a programmable microprocessor, which microprocessor may be programmed to operate the blood processing device 110, 210 according to a process.

According to other embodiments, the controller may include one or more electrical circuits designed to carry out the actions described herein. In fact, the controller may include a microprocessor and other circuits or circuitry. In addition, the controller may include one or more memories. The instructions by which the microprocessor is programmed may be stored on the memory associated with the microprocessor, which memory/memories may include one or more tangible non-transitory computer readable memories, having computer executable instructions stored thereon, which when executed by the microprocessor, may cause the microprocessors to carry out one or more actions as described below.

The controller may be coupled to one or more of the structures of the blood processing device, for example to receive information (e.g., in the form of signals) from these structures or to provide commands (e.g., in the form of signals) to these structures to control the operation of the structures. The controller may be coupled to the scales, sensors, clamps to provide commands to those devices to control their operation. It may also be possible that the controller receives information from and provides commands to a given structure, such as one of the structures already mentioned. The controller may be directly electrically connected to these structures to be coupled to them, or the controller may be directly connected to other intermediate equipment that is directly connected to these structures to be coupled to them. Finally, the controller is configured to communicate with one or more other devices such as a remote computer from which updated protocols can be retrieved by the controller of the blood processing device.

The device 10 includes a centrifuge 14 (FIG. 5) used to centrifugally separate blood components. The device 10 may be programmed to separate blood into a variety of components and sub-components. For example, in an exemplary blood separation procedure, the centrifuge 14 is operated to separate whole blood and collect mononuclear cells from the generated buffy coat.

A user interface screen 62 (e.g., a touchscreen) may be positioned above the front panel 52 (as in FIG. 3) or at some other location. The user interface screen 62 may allow an operator to interact with the system controller (e.g., a microprocessor) of the device 10 to provide instructions to the controller (e.g., to carry out a particular procedure), as well as providing information to the controller to be used during a procedure (e.g., white blood cell (WBC) pre-count of the blood of the blood source). The user interface screen 62 may provide the operator with instructions (e.g., to connect or disconnect the blood source from the flow circuit 12) and information (e.g., alerting the operator to a blockage in a fluid flow conduit of the flow circuit 12).

The blood processing device 110,210 may include computer equipment that permits the blood processing device 110, 210 including the controller 160, 260 to communicate (whether via wires, cables, etc. or wirelessly) with other blood processing devices over a local network, or with other blood processing devices or other computer equipment (e.g., a server) over local networks, wide area networks, or the Internet. According to such an embodiment, the input may include an internal transmitter/receiver device.

As noted, the various components of the fluid flow circuit 12 may be connected by flexible tubing or any other suitable fluid flow conduit. The illustrated flow circuit 12 is a "two needle" system, which includes a pair of blood source access devices 64 and 66 (e.g., phlebotomy needles), with one serving to draw blood into the flow circuit 12 from a source, while the other serves to return fluid to the source. In other embodiments, the flow circuit may be configured as a "single needle" system in which a single blood source access device (e.g., a phlebotomy needle) is used to both draw blood from a blood source and convey fluid to the blood source.

To begin a separation procedure, an operator may select (e.g., using the user interface screen 62) the procedure from among the variety of procedures that the device 10 is capable of performing. The operator may enter a variety of information requested by the system controller that allows the controller to better carry out the procedure. The controller can be provided with the total blood volume of the blood source, a WBC pre-count or the initial WBC concentration of the blood of the blood source, and a WBC post-count or a target platelet concentration to be achieved for the blood of the blood source by the end of the procedure. The total amount of blood to be processed may also be provided to the system controller. Additionally, various patient measurements such as height, weight, etc. may also be added.

When the system controller has received all of the necessary input, performed the necessary preliminary calculations and status checks (e.g., to confirm that the flow circuit 12 is properly installed and that the various components of the device 10 are functioning properly), and primed the flow circuit 12, the separation procedure may begin.

The system controller instructs one or more of the pumps of the device to draw blood from the blood source (donor/ patient) into a separation chamber. The blood enters the separation chamber and the buffy coat or mononuclear cell(MNC)-containing fraction is separated from the other blood components, with some or all of the other components being collected or returned to the source while the volume of the buffy coat or MNC-containing within the separation chamber increases. As noted above, the configuration of the separation chamber and the manner in which the buffy coat or MNC-containing fraction is separated from the other blood components may vary without departing from the scope of the present disclosure.

Blood draw and separation continue until they are ended by the system controller. The selected components are harvested or collected, while the other components of the blood are returned to the donor.

Having thus described the system and method in general terms, the details of the system and method are described in detail.

As mentioned above, the blood processing devices 110, 210 disclosed herein typically include a reusable separation apparatus and one or more disposable processing circuits adapted for association with the reusable apparatus, which apparatus and circuit(s) define the processor. The reusable separation apparatus may be any apparatus that can provide for the automated processing of biological fluid. "Biological fluid" includes without limitation blood and blood components, and "cell" or "biological cell" includes without limitation blood cells, such as red cells, white cells and platelets. By "automated," it is meant that the apparatus can be programmed to carry out the processing steps of a biological fluid processing method without substantial operator involvement. Of course, even in the automated system of the present disclosure, it will be understood that operator activity may be involved, including the loading of the disposable fluid circuits and entering processing parameters. Additional manual steps may be required as well. However, the reusable apparatus can process biological fluid through the disposable circuit(s) described below without substantial operator intervention.

The illustrated device is typically capable of effecting the separation of a biological fluid that includes biological cells into two or more components or fractions.

Before the operation of a blood processing device 110, 210, as mentioned above, a user or operator may select a procedure from a display screen that may contain a plurality of procedure options. This selection may be based on what the blood component will be utilized for.

The described blood processing devices 110,210 may be utilized as a method of collecting blood components which will be enhanced and/or modified by therapeutic cell manufacturers before being reintroduced into a patient. The blood component may be altered or modified by a manufacturer for a particular therapy. Optionally, the operator is able to select a particular manufacturer's specific procedure that operates according to a specific protocol.

This specific protocol may be determined by a number of factors that then determine the protocol parameters. The factors may include the specific therapy that will be provided to the patient (for example, CAR (T-cell therapy)) and the specific manufacturer of the modified drug. These factors may directly influence the protocol parameters that are used. The parameters may include a variety of different inputs.

According to an embodiment, process parameters may be in the form of, for example: a default value (e.g., 100 mL/min); a minimum (e.g., 20 mL/min); or a maximum (e.g., 100 mL/min). The parameters may include any parameter able to regulate a blood component collection procedure. The parameters can include measurements such as total blood volume for the process, harvest offsets, required consumables, and dilution amount for the collected component.

Because of the variation in process parameters and collection protocol, it is important for the manufacturers of the modified therapeutic cells, who are using the collected blood components, to be able to exhibit some control over the blood collection process so that the product that is obtained for subsequent modification/enhancement is able to be utilized by the manufacturer. The manufacturers are not in control of, or near the blood collection facilities, so it is important that there is a way to update the collection protocols on the blood processing device 110, 210 remotely.

In one embodiment, each blood processing device 110, 210 is connected to a remote computing device 120,220. The remote computing device 120,220 is able to store specific collection protocols from a variety of manufacturers, which can be accessed by an operator when operating the blood processing (apheresis) device 110,210. In this sense, remote suggests a geographic separation of the blood processing device 110,210 and remote computing device 120,220, the blood processing device 110, 210 and the remote computing device 120, 220 are disposed in separate rooms, buildings or laboratories, or even in different cities, countries, etc. The remote computing device 120,220 may be a server, "the cloud" or a web-based network.

In some embodiments, the remote computing device 120, 220 may be configured to store data from additional computing devices 140, 240, 250, 270. These additional computing devices 140, 240, 250, 270 may be at a plurality of different manufacturers in different geographical locations. By collecting procedure data from such a wide variety of additional computing devices 140, 240, 250, 270, the remote computing device 120, 220 can host a number of procedure protocols. A user may use the additional computing device 140 to generate or build a protocol from a plurality of different parameters, settings, processes, methods, configurations, etc. which can be stored on the remote computing device 120, 220.

The additional computing device or devices 140, 240, 250, 270 can be located at each manufacturing facility or a location easily accessible by each of the drug manufacturers. In one embodiment, each additional computing device 140 is at least one of the group consisting of a personal computer, tablet, laptop, or cellular phone. However, the additional computing device 140 may be any such device capable of inputting instructions or protocols and transferring such protocols, whether by network or email or another method.

Once a protocol is generated by a user at additional computing device 140, the protocol may be transmitted, downloaded or otherwise sent from the additional computing device 140 to the remote computing device 120, 220 and then to one or more blood processing devices 110, 210. The remote computing device 120,220 may be configured to store the generated protocol in a database or library of protocols for future use. Each of the blood processing devices 110, 210 may further be configured to store a plurality of protocols generated locally at the device or remotely at the remote computing device 120,220. A user interface (e.g., 62) of the blood processing device 110,210 may be used by an operator to upload and select a particular protocol designated by manufacturer.

According to certain embodiments, the remote computing device 120,220 may be configured to alter the operation of the associated blood processing device 110,210 in accordance with current protocol for the selected procedure. In particular, the remote computing device 120,220 may be configured to alter the operation of one or more associated blood processing devices in a centralized manner, for example by altering the configuration (e.g., programming) of the controller(s) associated with multiple blood processing devices (such as by downloading a protocol or process including at least one process parameter or process parameter control to one or more of the blood processing devices). In this regard, the remote computing device 120,220 may have computer executable instructions stored thereon (e.g., in one or more tangible non-transitory computer-readable memories), which when executed by the blood processing device (or more particularly, the controllers of the blood processing device), may cause the blood processing device 110,210 to apply at least one process parameter (or at least one process parameter control). According to one embodiment, the controller 160,260 of the blood processing device 110,210 has stored thereon a plurality of process parameters or process parameter controls, which process parameters or process parameter controls may define one or more processes to be carried out using the blood processing device 110,210. The remote computing device 120,220 may also be configured to transmit one or more process parameters to one or more blood processing device 110,210.

According to certain embodiments, the remote computing device 120,220 may include a control mechanism that drives protocols and respective elements stored and sends them to the blood processing device 110,210 when a protocol is generated and distribution is sought. For example, the remote computing device 120,220 may include logic (e.g., in the form of hardware, programming, or both) that may limit the total number of protocols distributed to one or more of the blood processing devices. In addition, the remote computing device 120,220 may include logic that controls which protocols are sent to which blood processing devices. The blood processing devices, specifically the controller, receive these updated protocols from the remote computing device 120,220. The controller of the blood processing device 110,210 can store these protocol for use. Upon receiving a new protocol for a manufacturer/therapy, the blood processing device 110,210 may delete old or out of date therapy protocols.

In some embodiments, protocol generation at additional computing device 140 may be limited by output data from an evaluation algorithm which is configured to indicate whether a procedure is feasible or not feasible. For example, an operator may enter a plurality of parameters at the additional computing device 140. The computing device 140 may be configured to operate an evaluation algorithm on the parameters to estimate one or more features of the protocol, such as a time to completion, a yield of a particular biological component, a use of a material such as a supernatant, etc. The evaluation algorithm may generate output data such as a notification, alert, caution, etc., which indicates that the selected parameters will result in an infeasible protocol. The evaluation algorithm may further provide an indication of the infeasibility (e.g., time to completion of protocol would exceed a predetermined time) and may further provide a recommended modification to a parameter that would make the protocol feasible.

The protocol update to the remote computing device 120,220 may require authorization. This may occur at the additional computing device 140 or the remote computing device 120,220. The remote computing device 120,220 may be configured to determine if a user has authorization that permits the user to enter and/or modify the process parameters (and/or to enter and/or modify process parameters within a controlled range) and/or (ii) enter and/or modify process parameter controls. This determination may be made any time a user attempts to enter or modify process parameters, or the determination may be made only when a user attempts to enter or modify a process parameter control, according to certain embodiments. Authorization may be provided based on an identifier provided by a user.

It will be recognized that the use of an alphanumeric password or passcode as an identifier is only one possible embodiment. According to other embodiments, the identifier may be a two-dimensional or three-dimensional barcode printed on a badge or key that is read. As another embodiment, the identifier may be stored on a memory storage device, such as may be carried on a badge or card, that can form an electrical and/or magnetic communication link with the memory storage device to read the identifier stored thereon. Other possible embodiments also exist.

While the foregoing embodiments of the present disclosure discuss operation of a single blood processing device, the systems and methods of retrieving and updating protocols may also be applied to a network of blood processing devices coupled to a remote computing device 120, 220 and at least one additional computing device 140 to define a system of connected systems (or nodes), which system may also be referred to as a network according to certain embodiments. The network may be a local network, a wide area network, or the Internet, for example, and may be implemented via wires/cables or wirelessly. As illustrated, the devices may communicate with the remote computing device 120, 220, or vice versa (i.e., the communication is bi-directional), although the communication may be predominantly or exclusively uni-directional according to other embodiments.

In some embodiments, the remote computing device 120, 220 may be configured to provide one or more data management services relative to the blood processing devices 110, 210. In particular, the remote computing device 120, 220 may provide the ability to view, analyze, and/or track data related to blood collection procedures. In addition, or in the alternative, the remote computing 120, 220 device may provide the ability to view, analyze and/or track data separate and apart from the blood collection procedures or other additional data.

For instance, the remote computing device 120, 220 may be configured to receive from one or more of the blood processing devices 110, 210 procedure data relating to a procedure performed by a blood processing device 110, 210. The procedure data may comprise operator interactions with the blood processing device 110, 210 that the blood processing device has sensed or otherwise determined have occurred (e.g., connecting a wash medium, connecting a source container of biological fluid, taking a cell suspension sample, or other operator interactions with the blood processing device). The procedure data may comprise information about disposable components (e.g., soft goods or other consumable materials) used in the procedure, such as a lot number, reference number, expiration date, product code, type, size, or other data about a disposable component. The procedure data may comprise an indication of an operation performed by the blood processing device (e.g., a wash process, a spinning process, delivering a wash medium from its container, separating supernatant, etc.). The procedure data may comprise a system notification, alarm, or alert generated by a blood processing device 110, 210 to provide information to an operator of the occurrence of an event (e.g., improper loading of a disposable component, operation complete, operator interaction required, etc.). The procedure data may comprise an identifier of one or more persons who have controlled the blood processing device 110, 210 to perform an operation and may further comprise an indication of their authorization level. Any one or more of these procedure data may be recorded on the blood processing device 110, 210 for later retrieval, e.g., via a report, and may further be transmitted to the remote computing device 120, 220 for retrieval, observation, reporting, etc. Procedure data may be stored in a database, for example a relational database management system, for later retrieval. Users may also be able to retrieve this information/data on the additional computing devices 140, 240, 250, 270.

Thus, an improved method and system have been disclosed for the collecting blood components. The description provided above is intended for illustrative purposes only and is not intended to limit the scope of the invention to any specific method, system, or apparatus, or device described herein except as may be explicitly delineated above.

Aspects

Aspect 1. A blood processing system, comprising: a blood processing device with a controller configured to operate the blood processing device based on a plurality of collection protocols; a remote computing device wirelessly connected to the blood processing device, said remote computing device configured to maintain a plurality of collection protocols; and at least one additional computing device; wherein the at least one additional computing device is configured to update one or more of the plurality of collection protocols on said remote computing device by communicating changes to a protocol maintained on the remote computing device which updates the plurality of collection protocols at the controller of the blood processing device.

Aspect 2. The blood processing system of Aspect 1, wherein the blood processing device is an apheresis machine.

Aspect 3. The blood processing system of any of the preceding Aspects, wherein the plurality of collection protocols specify the blood component collected by the blood processing device.

Aspect 4. The blood processing system of any of the preceding Aspects, wherein each of the plurality of collection protocols specifies at least one collection parameter.

Aspect 5. The blood processing system of Aspect 4, wherein the collection parameter is at least one of the group consisting of total blood volume collected, collection offset, cycle volumes, dilution amounts, and final product volumes.

Aspect 6. The blood processing system of any of the preceding Aspects, wherein the remote computing device is a server.

Aspect 7. The blood processing system of any of the preceding claims, wherein the at least one additional computing device is at least one of the group consisting of a personal computer, tablet, laptop, or cellular phone.

Aspect 8. The blood processing system of any of the preceding Aspects, wherein the at least one additional computing device is at least two additional computing devices.

Aspect 9. A method of collecting blood components from a donor, comprising providing a collection protocol to a computing device; communicating the collection protocol from said computing device to a remote computing device; communicating the collection protocol from said remote computing device to a controller of a blood processing device; selecting a collection protocol from an interface on the blood processing device; connecting the blood processing device to a patient; and starting the blood collection based on the selected collection protocol.

Aspect 10. The method of Aspect 9, further comprising inputting designated patient measurements based on collection protocol requirements.

Aspect 11. The method of Aspect 9 or 10, further comprising updating the collection protocol at a computing device, communicating the updated collection protocol from the computing device to a remote computing device, and communicating the updated collection protocol from the remote computing device to the controller of the blood processing device, wherein the updated collection protocol replaces the collection protocol.

Aspect 12. The method of Aspect 11, further comprising selecting an updated collection protocol from an interface on the blood processing device, inputting designated updated collection protocol parameters, and starting the blood collection based on the selected updated collection protocol.

Aspect 13. The method of Aspect 11 or 12, wherein the updated collection protocol include different collection protocol parameters than the collection protocol parameters.

Aspect 14. The method of any of Aspects 9-13 wherein the collection protocol parameters include at least one of the group consisting of total blood volume collected, collection offset, cycle volumes, dilution amounts, and final product volumes.

Aspect 15. The method of any of Aspects 9-14 further comprising collecting a first blood component based on the collection protocol.

Aspect 16. The method of Aspect 15, wherein the blood processing device is an apheresis machine and the method further comprises returning a second blood component to the patient.

Aspect 17. The method of any of Aspects 9-16, wherein the remote computing device is a wirelessly connected server.

Aspect 18. The method of any of Aspects 9-17, wherein the computing device is at least It will be understood that the embodiments and examples described above are illustrative of some of the applications of the principles of the present subject matter. Numerous modifications may be made by those skilled in the art without departing from the spirit and scope of the claimed subject matter, including those combinations of features that are individually disclosed or claimed herein. For these reasons, the scope hereof is not limited to the above description but is as set forth in the following claims, and it is understood that claims may be directed to the features hereof, including as combinations of features that are individually disclosed or claimed herein.

The invention claimed is:

1. A blood processing system, comprising:
a blood processing device with a controller configured to operate the blood processing device based on a plurality of collection protocols;
a remote computing device wirelessly connected to the blood processing device, said remote computing device configured to maintain a plurality of collection protocols from a variety of manufacturers, which can be accessed by an operator when operating the blood processing device; and
at least one additional computing device, accessible by at least one of the variety of manufacturers, which is configured to generate a collection protocol and transfer the collection protocol to the remote computing device;
wherein the at least one additional computing device is configured to update one or more of the plurality of collection protocols on said remote computing device by communicating changes to a protocol maintained on the remote computing device which updates the plurality of collection protocols at the controller of the blood processing device.

2. The blood processing system of claim 1, wherein the blood processing device is an apheresis machine.

3. The blood processing system of claim 1, wherein the plurality of collection protocols specify the blood component collected by the blood processing device.

4. The blood processing system of claim 1, wherein each of the plurality of collection protocols specifies at least one collection parameter.

5. The blood processing system of claim 4, wherein the collection parameter is at least one of the group consisting of total blood volume collected, collection offset, cycle volumes, dilution amounts, and final product volumes.

6. The blood processing system of claim 1, wherein the remote computing device is a server.

7. The blood processing system of claim 1, wherein the at least one additional computing device is at least one of the group consisting of a personal computer, tablet, laptop, or cellular phone.

8. The blood processing system of claim 1, wherein the at least one additional computing device is at least two additional computing devices.

9. The blood processing system of claim 1, wherein the plurality of collection protocols includes protocols, which are based on an intended drug therapy.

10. The blood processing system of claim 1, wherein the plurality of collection protocols includes protocols, which are based on a manufacturing facility.

11. The blood processing system of claim 1, wherein the at least one additional computing device includes a plurality of additional computing devices at a plurality of different manufacturers in different geographical locations.

* * * * *